United States Patent [19]

Samain et al.

[11] Patent Number: 5,538,517
[45] Date of Patent: Jul. 23, 1996

[54] METHOD FOR DYEING KERATIN FIBERS WITH INDOLE OR INDOLINE DERIVATIVES, HYDROGEN PEROXIDE AND A PEROXIDASE

[75] Inventors: Henri Samain, Bièvres; Claude Dubief, Le Chesnay, both of France

[73] Assignee: L'Oreal, Paris, France

[21] Appl. No.: 360,850

[22] PCT Filed: Jun. 22, 1993

[86] PCT No.: PCT/FR93/00617

§ 371 Date: Mar. 8, 1995

§ 102(e) Date: Mar. 8, 1995

[87] PCT Pub. No.: WO94/00100

PCT Pub. Date: Jan. 6, 1994

[30] Foreign Application Priority Data

Jun. 25, 1992 [FR] France ................................ 92 07784

[51] Int. Cl.⁶ ............................ A61K 7/13; C09B 67/00
[52] U.S. Cl. .......................... 8/423; 8/401; 8/406; 8/407; 8/408; 8/409
[58] Field of Search ..................... 8/401, 405, 406, 8/423, 435, 407, 408, 409

[56] References Cited

U.S. PATENT DOCUMENTS

| | | | |
|---|---|---|---|
| 3,893,803 | 7/1975 | Kaiser | 8/408 |
| 3,957,424 | 5/1976 | Zeffren et al. | 8/10.2 |
| 3,993,436 | 11/1976 | Fujinuma | 8/10.2 |
| 4,515,773 | 5/1985 | Herlihy | 424/59 |
| 4,609,544 | 9/1986 | Herlihy | 424/59 |
| 4,961,925 | 10/1990 | Tsujino et al. | 8/402 |
| 5,131,911 | 7/1992 | Lang et al. | 8/423 |
| 5,207,798 | 5/1993 | Cotteret et al. | 8/423 |
| 5,244,497 | 9/1993 | Junino et al. | 8/423 |

FOREIGN PATENT DOCUMENTS

| | | |
|---|---|---|
| 0441689 | 8/1991 | European Pat. Off. |
| 2112550 | 6/1972 | France |
| 2252841 | 8/1991 | France |
| 53-32132 | 3/1978 | Japan |

Primary Examiner—Paul Lieberman
Assistant Examiner—Caroline L. Dusheck
Attorney, Agent, or Firm—Cushman Darby & Cushman

[57] ABSTRACT

A method for dyeing keratin fibers by applying thereto: a component (1) consisting of an aqueous dyeing medium containing a compound of formula

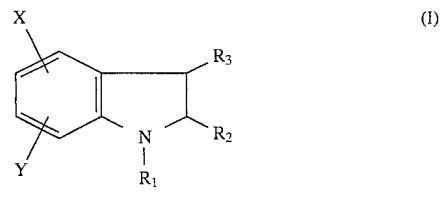

(I)

or

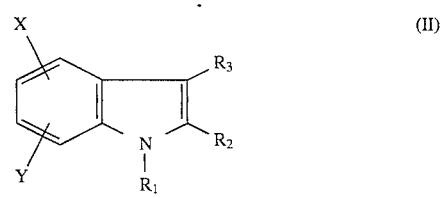

(II)

wherein $R_1$ is hydrogen or alkyl; $R_2$ is hydrogen, alkyl or COOH; $R_3$ is hydrogen or alkyl; X is hydrogen, OH, $NH_2$, alkyl or alkoxy; and Y is OH or $NH_2$; a component (2) consisting of an aqueous dyeing medium containing a peroxidase enzyme; and a component (3) containing hydrogen peroxide or an enzymatic hydrogen peroxide source; said component (1) being applied first and separately from component (3).

37 Claims, No Drawings

METHOD FOR DYEING KERATIN FIBERS WITH INDOLE OR INDOLINE DERIVATIVES, HYDROGEN PEROXIDE AND A PEROXIDASE

The invention relates to a method for dyeing keratin fibers using indole or indoline derivatives, hydrogen peroxide and a peroxidase enzyme.

The so-called "permanent" coloration of the hair consists in obtaining a coloration which is visible on the hair for several weeks, and which is shampoo-resistant.

For this, it is possible to use indole or indoline precursors which are liable to become oxidized in the presence of an oxidizing agent to give colored products, the chemical structure of which is similar to hair pigments such as melanin.

The oxidizing agent commonly used is hydrogen peroxide.

Oxidation dye precursors chosen from indole or indoline derivatives have the advantage of producing colorations which are close to the natural shades.

The oxidation dyeing methods of the state of the art, using indole- or indoline-type precursors and hydrogen peroxide as the oxidizing system, are generally carried out in alkaline dyeing media in order to obtain satisfactory dyeing properties. However, the application of these alkaline media results in degradation of the fibers.

The Applicant has just discovered, surprisingly, a novel method for the oxidation dyeing of keratin fibers, based on indole or indoline derivatives, which, after oxidation with hydrogen peroxide in the form of an aqueous hydrogen peroxide solution or produced by a natural enzymatic source, in the presence of a peroxidase enzyme, made it possible to obtain, under mild pH conditions, strong colorations which are shampoo-resistant, without degradation of the fibers.

The subject of the invention is thus a novel method of dyeing using at least one indole or indoline derivative, hydrogen peroxide and a peroxidase enzyme.

Another subject of the invention consists of the compositions and multi-compartment devices used in the context of this method.

Other subjects will become apparent on reading the description and the examples which follow.

The method for dyeing keratin fibers and in particular the hair, in accordance with the invention, is characterized in that at least the following are applied to these fibers:

a component (1) containing, in an aqueous medium which is suitable for dyeing, at least one compound of formula:

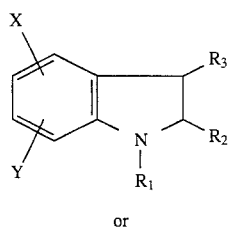

or

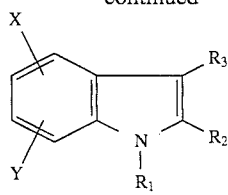

in which:
$R_1$ represents a hydrogen atom or a $C_1$–$C_4$ alkyl radical;
$R_2$ represents a hydrogen atom, a $C_1$–$C_4$ alkyl radical or —COOH;
$R_3$ represents a hydrogen atom or a $C_1$–$C_4$ alkyl radical;
X denotes a hydrogen atom, $NH_2$, OH, a $C_1$–$C_4$ alkyl radical or a $C_1$–$C_4$ alkoxy radical;
Y denotes OH or $NH_2$;
with the proviso that when X denotes OH or alkyl, X occupies positions 5, 6 or 7 and X is in an ortho position relative to Y;

a component (2) containing, in an aqueous medium which is suitable for dyeing, at least one peroxidase enzyme;

a component (3) containing, in an aqueous medium which is suitable for dyeing, at least hydrogen peroxide or an enzymatic source of hydrogen peroxide;

the component (1) being applied to the fibers first, separately from the component (3).

Among the preferred indole or indoline precursors of formula (I) or (II), there may be mentioned 5,6-dihydroxyindole, 2-methyl-5,6-dihydroxyindole, 3-methyl-5,6-dihydroxyindole, 4-hydroxyindole, 2,3-dimethyl-5,6-dihydroxyindole, 6-hydroxy-5-methoxyindole, 6-hydroxyindole, 5-hydroxyindole, 7-hydroxyindole, 7-aminoindole, 5-aminoindole, 5,6-dihydroxyindole-2-carboxylic acid, 4-aminoindole, 1-methyl-5,6-dihydroxyindole, 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline, 5-methoxy-6-hydroxyindoline and the salts thereof.

The peroxidase enzyme used in accordance with the invention is an enzyme of code number 1.11.1. according to the enzyme classification system (Enzyme Nomenclature, 1984, Academic Press Inc.).

Examples which may be mentioned are peroxidases derived from natural sources such as horseradish, turnip, fig, cow's milk or soya. They are used according to the invention in varying degrees of purification and in amounts which vary depending on the degree of purity.

Peroxidases derived from horseradish, such as the products sold by the company Sigma, are especially used.

The peroxidases in accordance with the-present invention are used in amounts between 100 and 40,000 catalytic units of peroxidase per 100 g of components (1), (2) and (3), as defined above, to be applied to the hair; the catalytic units being determined during the reaction for the oxidation of pyrogallol by hydrogen peroxide at pH 6 and at 20° C. (one catalytic unit enables 1 mg of pyrogallol to be converted into purpurogallin in 20 seconds).

In the case where hydrogen peroxide in the form of an aqueous hydrogen peroxide solution is used as the oxidizing agent, the amounts of peroxidase are preferably between 1,000 and 20,000 catalytic units.

The enzymatic sources of hydrogen peroxide in accordance with the present invention consist of one or more natural substrates(s) associated with one or more oxidase-type enzymatic system(s) which catalyze the oxidation of a substrate molecule by an oxygen molecule by transfer of a single oxygen atom.

Among the natural substrates used, there may be mentioned glucose, uric acid, alcohols, amino acids and lactic acid. They are used at concentrations preferably between 1 and 25% by weight and more particularly between 3 and 15% by weight relative to the total weight of the component or components (2) and/or (3).

The oxidase-type enzymatic systems according to the invention are chosen from the oxidases of code number 1.x.3, which catalyze the oxidation of a substrate molecule by an oxygen molecule by transfer of a single atom from the oxygen molecule. The amounts used are determined depending on their purity. They preferably vary between 100 and 20,000 catalytic units of oxidase per 100 g of components (1), (2) and (3) to be applied to the keratin fibers; the units being determined in the reaction for the air oxidation of the substrate at pH 5.1 and at 37° C. (one unit of oxidase enables 1 µg of substrate to be converted in 1 minute).

Among the systems natural substrate/enzyme for the oxidation of the substrate by oxygen by transfer of a single oxygen atom, there may be mentioned:

glucose/glucose oxidase galactose/galactose oxidase pyranose/pyranose oxidase

L-sorbose/L-sorbose oxidase ethanol/alcohol oxidase (1.1.3.13)

isopropanol/secondary alcohol oxidase (1.1.3.18)

pyruvic acid/pyruvate oxidase oxalic acid/oxalate oxidase aspartic acid/aspartate oxidase glutamic acid/L-glutamate oxidase uric acid/uricase lactic acid/lactate oxidase, or mixtures thereof.

One embodiment of the invention consists in applying to the keratin fibers, in a first step, a composition (A) containing, in an aqueous medium which is suitable for dyeing, the component (1) as defined above and, in a second step, a composition (B) containing, in an aqueous medium which is suitable for dyeing, at least the components (2) and (3) as defined above.

A rinsing operation may be carried out between the two applications.

The application period of the first composition (A) preferably ranges between 20 seconds and 20 minutes when the component (3) contains an aqueous hydrogen peroxide solution or from 1 minute to 1 hour when the component (3) contains an enzymatic source of hydrogen peroxide, and that of the second composition (B) preferably ranges between 1 minute and 1 hour and more particularly between 5 minutes and 20 minutes.

A second embodiment of the invention consists in successively applying to the fibers a first composition (C) containing the components (1) and (2), followed by a second composition (D) containing, in a medium which is suitable for dyeing, the component (3). The application period of the composition (C) preferably ranges between 20 seconds and 20 minutes, that of the composition (D) preferably ranges between 1 minute and 1 hour and more particularly between 5 minutes and 20 minutes.

A third embodiment of the invention consists in successively applying to the fibers a composition (E) containing the component (1), a composition (F) containing the component (2) and a composition (G) containing the component (3).

The application periods of the compositions (E) and (F) preferably range between 20 seconds and 20 minutes, that of the composition (G) preferably ranges between 1 minute and 1 hour and more particularly between 5 minutes and 20 minutes.

Depending on the various forms of the dyeing methods of the invention, a final rinsing operation and a drying operation may be carried out at the end of the treatment.

The compositions used in these processes have pHs preferably between 3 and 10 and more particularly between 4.5 and 7.5.

The basifying agents which may be used in these compositions may in particular be amines such as alkanolamines, alkylamines, and ammonium or alkali metal carbonates or hydroxides.

The acidifying agents which may be used in the compositions of the invention may be chosen from lactic acid, acetic acid, tartaric acid, phosphoric acid, hydrochloric acid and citric acid.

The dyeing compositions (A), (C) and (E) as defined above contain indole or indoline derivatives of formula (I) or (II) in concentrations preferably between 0.2 and 5% by weight relative to the total weight of each of these compositions.

They may additionally contain a co-solvent chosen from lower alcohols such as ethyl alcohol or isopropanol; glycol ethers such as the monomethyl, monoethyl or monobutyl ethers of ethylene glycol or of diethylene glycol, the monomethyl ethers of propylene glycol and of dipropylene glycol; glycol esters such as the monomethyl ether acetate or the monoethyl ether acetate of ethylene glycol; glycols such as ethylene glycol and propylene glycol; lower esters such as methyl lactate.

The preferred solvents are ethyl alcohol and propylene glycol.

The solvents are present in concentrations preferably between 0.5 and 75% and in particular between 2 and 50% by weight relative to the total weight of the composition.

The dyeing compositions according to the invention may contain other dyes usually used for dyeing keratin fibers, in particular direct dyes such as nitrobenzene derivatives, azo dyes, anthraquinones, naphthoquinones and benzoquinones or oxidation dyes of the para or ortho type and/or coupling agents.

The oxidizing compositions of the invention, such as the compositions (B), (D) or (G) as defined above, contain hydrogen peroxide in amounts between 0.03 and 10% and preferably between 0.05 and 5% by weight relative to the total weight of one of these compositions.

The compositions used in the various dyeing methods of the invention may additionally contain various adjuvants such as anionic, cationic, nonionic or amphoteric surface-active agents or mixtures thereof, thickening agents, fragrances, sequestering agents, agents for treating keratin fibers, dispersing agents, conditioning agents, agents for swelling keratin fibers, and preserving agents.

The compositions used in the various dyeing methods of the invention may be in the form of lotions which are thickened to a greater or lesser extent, gels or emulsions.

For the purpose of implementing the various forms of the dyeing method according to the invention, the compositions may be packaged in multi-compartment devices also referred to as "kit" or "dyeing equipment", containing all of the components (1), (2) and (3) intended to be applied in the same dyeing operation to keratin fibers.

According to a first embodiment, the dyeing equipment or kit comprises a first compartment containing a composition (A) as defined above and a second compartment containing a composition (B) as defined above.

Another embodiment consists of a dyeing kit containing, in a first compartment, a composition (C) and, in a second compartment, a composition (D) as defined above.

Another embodiment consists of a dyeing kit comprising three compartments, of which one contains a composition (E), the second contains a composition (F) and the third contains a composition (G).

The examples which follow are intended to illustrate the invention without, however, being limiting in nature.

EXAMPLES OF COMPOSITIONS

EXAMPLE 1

| Composition (A1) | |
| --- | --- |
| 5,6-Dihydroxyindole | 1 g |
| Ethyl alcohol | 10 g |
| Demineralized water | qs 100 g |
| The pH of the solution is 6.4. | |
| Composition (B1) | |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 5.1 |
| Demineralized water | qs 100 g |

The first composition is applied to the hair and is left in place for 15 minutes. The hair is rinsed. The second composition is applied, leaving it in place for 15 minutes. The hair is rinsed. It is noted after shampooing that the hair, which was initially white, is chestnut in color. The shade obtained easily resists shampooing several times.

EXAMPLE 2

| Composition (A2) | |
| --- | --- |
| 5,6-Dihydroxyindole | 0.5 g |
| Ethyl alcohol | 10 g |
| Demineralized water | qs 100 g |
| The pH of the solution is 6.5. | |
| Composition (B2) | |
| Horseradish peroxidase | 1,300 units |
| 20 volumes aqueous hydrogen peroxide solution (acidified to pH 2 with orthophosphoric acid) | 62 g |
| Monoethanolamine | qs pH = 5.5 |
| Demineralized water | qs 100 g |

The same method is used as for Example 1. It is noted after shampooing that the hair, which was initially white, is light brown in color.

EXAMPLE 3

| Composition (C3) | |
| --- | --- |
| 5,6-Dihydroxyindole | 1.5 g |
| Horseradish peroxidase | 3,000 units |
| Ethyl alcohol | 10 g |
| Demineralized water | qs 100 g |
| The pH of the solution is 6.5. | |
| Composition (D3) | |
| 20 volumes aqueous hydrogen peroxide solution (acidified to pH 2 with orthophosphoric acid) | 12 g |
| Monoethanolamine | qs pH = 6 |
| Demineralized water | qs 100 g |

The first composition is applied to the hair and is left in place for 5 minutes. Without rinsing, the second composition is applied and is left in place for 20 minutes. It is noted after shampooing that the hair, which was initially white, is chestnut in color.

EXAMPLE 4

| Composition (E4) | |
| --- | --- |
| 5,6-Dihydroxyindole | 1 g |
| Ethyl alcohol | 10 g |
| Demineralized water | qs 100 g |
| The pH of the solution is 6.5. | |
| Composition (F4) | |
| Horseradish peroxidase | 3,000 units |
| Demineralized water | qs 100 g |
| Composition (G4) | |
| 20 volumes aqueous hydrogen peroxide solution (acidified to pH 2 with orthophosphoric acid) | 2.5 g |
| Monoethanolamine | qs pH = 6 |
| Demineralized water | qs 100 g |

The first composition is applied to the hair and is left in place for 5 minutes. The hair is rinsed. The second composition is applied to the hair and is left in place for 5 minutes. The third composition is applied, and is left in place for 15 minutes. The hair is rinsed. It is noted after shampooing that the hair, which was initially white, is chestnut in color.

EXAMPLE 5

| Composition (A5) | |
| --- | --- |
| 2-Methyl-5,6-dihydroxyindole hydrobromide | 1 g |
| Ethyl alcohol | 10 g |
| Triethanolamine | qs pH = 7 |
| Demineralized water | qs 100 g |
| Composition (B5) | |
| Horseradish peroxidase | 2,600 units |
| 20 volumes aqueous hydrogen peroxide solution (acidified to pH 2 with orthophosphoric acid) | 2.5 g |
| Triethanolamine | qs pH = 5.5 |
| Demineralized water | qs 100 g |

The same method is used as in Example 1. A light brown coloration is obtained on hair which was initially white.

EXAMPLE 6

| Composition (A6) | |
| --- | --- |
| 3-Methyl-5,6-dihydroxyindole | 1 g |
| Ethyl alcohol | 10 g |

| Preserving agent | qs |
| --- | --- |
| Triethanolamine | qs pH = 6.8 |
| Demineralized water | qs 100 g |

| Composition (B6) | |
| --- | --- |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 5.5 |
| Demineralized water | qs 100 g |

The same method is used as in Example 1. A chestnut coloration is obtained on hair which was initially white.

EXAMPLE 7

| Composition (A7) | |
| --- | --- |
| 4-Hydroxyindole | 1 g |
| Ethyl alcohol | 10 g |
| 20 % aqueous ammonia | qs pH = 7 |
| Demineralized water | qs 100 g |

| Composition (B7) | |
| --- | --- |
| Horseradish peroxidase | 1,600 units |
| 20 volumes aqueous hydrogen peroxide solution (acidified to pH 2 with orthophosphoric acid) | 2.5 g |
| Monoethanolamine | qs pH = 5.5 |
| Demineralized water | qs 100 g |

The same method is used as in Example 1. A chestnut coloration is obtained on hair which was initially white.

EXAMPLE 8

| Composition (A8) | |
| --- | --- |
| 2,3-Dimethyl-5,6-dihydroxyindole hydrobromide | 1 g |
| Ethyl alcohol | 10 g |
| Triethanolamine | qs pH = 7 |
| Demineralized water | qs 100 g |

| Composition (B8) | |
| --- | --- |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 5.5 |
| Demineralized water | qs 100 g |

The same method is used as in Example 1. A light brown coloration is obtained on hair which was initially white.

EXAMPLE 9

| Composition (A9) | |
| --- | --- |
| 6-Hydroxy-5,6-methoxyindole | 1 g |
| Ethyl alcohol | 10 g |
| Triethanolamine | qs pH = 5.5 |
| Demineralized water | qs 100 g |

| Composition (B9) | |
| --- | --- |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 5.5 |
| Demineralized water | qs 100 g |

The same method is used as in Example 1. A light brown coloration is obtained on hair which was initially white.

EXAMPLE 10

| Composition (A10) | |
| --- | --- |
| 6-Hydroxyindole | 1 g |
| Ethyl alcohol | 10 g |
| Triethanolamine | qs pH = 7 |
| Demineralized water | qs 100 g |

| Composition (B10) | |
| --- | --- |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 5.5 |
| Demineralized water | qs 100 g |

The same method is used as in Example 1. A chestnut coloration is obtained on hair which was initially white.

EXAMPLE 11

| Composition (A11) | |
| --- | --- |
| 5-Hydroxyindole | 1 g |
| Ethyl alcohol | 10 g |
| Triethanolamine | qs pH = 6.8 |
| Demineralized water | qs 100 g |

| Composition (B11) | |
| --- | --- |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 5.5 |
| Demineralized water | qs 100 g |

The same method is used as in Example 1. A dark blond coloration is obtained on hair which was initially white.

EXAMPLE 12

| Composition (A12) | |
| --- | --- |
| 7-Hydroxyindole | 1 g |
| Ethyl alcohol | 10 g |
| Triethanolamine | qs pH = 7 |
| Demineralized water | qs 100 g |

| Composition (B12) | |
| --- | --- |
| Horseradish peroxidase | 3,600 units |
| 20 volumes aqueous hydrogen peroxide solution (acidified to pH 2 with orthophosphoric acid) | 2.5 g |
| Monoethanolamine | qs pH = 5.5 |
| Demineralized water | qs 100 g |

The same method is used as in Example 1. An iridescent chestnut coloration is obtained on hair which was initially white.

EXAMPLE 13

| Composition (A13) | |
|---|---|
| 7-Aminoindole | 1 g |
| Ethyl alcohol | 10 g |
| Triethanolamine | qs pH = 5.6 |
| Demineralized water | qs 100 g |
| Composition (B13) | |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 5.5 |
| Demineralized water | qs 100 g |

The same method is used as in Example 1. A light brown coloration is obtained on hair which was initially white.

EXAMPLE 14

| Composition (A14) | |
|---|---|
| 5,6-Dihydroxyindole-2-carboxylic acid | 1 g |
| Ethyl alcohol | 10 g |
| Triethanolamine | qs pH = 7 |
| Demineralized water | qs 100 g |
| Composition (B14) | |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 5.5 |
| Demineralized water | qs 100 g |

The same method is used as in Example 1. A light brown coloration is obtained on hair which was initially white.

EXAMPLE 15

| Composition (A15) | |
|---|---|
| 5-Aminoindole | 1 g |
| Ethyl alcohol | 10 g |
| Demineralized water | qs 100 g |
| Composition (B15) | |
| Horseradish peroxidase | 3,000 units |
| 20 volumes aqueous hydrogen peroxide solution (acidified to pH 2 with orthophosphoric acid) | 2.5 g |
| Monoethanolamine | qs pH = 5.8 |
| Demineralized water | qs 100 g |

The same method is used as in Example 1. A chestnut coloration is obtained on hair which was initially white.

EXAMPLE 16

| Composition (A16) | |
|---|---|
| 4-Aminoindole | 0.5 g |
| Ethyl alcohol | 10 g |
| Triethanolamine | qs pH = 6.5 |
| Demineralized water | qs 100 g |
| Composition (B16) | |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 6 |
| Demineralized water | qs 100 g |

The same method is used as in Example 1. A chestnut coloration is obtained on hair which was initially white.

EXAMPLE 17

| Composition (A17) | |
|---|---|
| 1-Methyl-5,6-dihydroxyindole | 1 g |
| Ethyl alcohol | 10 g |
| Triethanolamine | qs pH = 7 |
| Demineralized water | qs 100 g |
| Composition (B17) | |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 5.9 |
| Demineralized water | qs 100 g |

The same method is used as in Example 1. A chestnut coloration is obtained on hair which was initially white.

EXAMPLE 18

A fresh horseradish tuber is finely ground by means of a mixer, a machine sold commercially as a food processor. The ground material is employed in the manufacture of the second composition of this example.

| Composition (A18) | |
|---|---|
| 5,6-Dihydroxyindole | 1 g |
| Ethyl alcohol | 10 g |
| Demineralized water | qs 100 g |
| The pH of the solution is 6.4. | |
| Composition (B18) | |
| Fresh ground horseradish | 10 g |
| 20 volumes aqueous hydrogen peroxide solution (acidified to pH 2 with orthophosphoric acid) | 2.5 g |
| Monoethanolamine | qs pH = 5.5 |
| Demineralized water | qs 100 g |

The first composition is applied to the white hair and is left in place for 15 minutes. The hair is rinsed. The second composition is applied and is left in place for 15 minutes. The hair is rinsed. It is noted after shampooing that the hair is chestnut in color.

EXAMPLE 19

| Composition (A19) | |
|---|---|
| 5,6-Dihydroxyindoline | 1 g |
| Ethyl alcohol | 10 g |
| Triethanolamine | qs pH = 7 |
| Demineralized water | qs 100 g |
| Composition (B19) | |
| Horseradish peroxidase | 2,600 units |
| 20 volumes aqueous hydrogen peroxide solution (acidified to pH 2 with orthophosphoric acid) | 2.5 g |
| Monoethanolamine | qs pH = 5.9 |
| Demineralized water | qs 100 g |

The same method is used as in Example 1. A chestnut coloration is obtained on hair which was initially white.

EXAMPLE 20

| Composition (A20) | |
|---|---|
| 5,6-Dihydroxyindole | 1.5 g |
| Triethanolamine | qs pH = 6.5 |
| Ethanol | 10 g |
| Demineralized water | qs 100 g |
| Composition (B20) | |
| Glucose | 10 g |
| Glucose oxidase | 15,000 units |
| Horseradish peroxidase | 2,600 units |
| Demineralized water | qs 100 g |
| The pH of this composition is 6.8. | |

The first composition is applied to a lock of hair, which is initially white, and is left in place for 15 minutes. The hair is rinsed. The second composition is applied and is left in place for 15 minutes. The procedure is completed by a final rinsing operation and a drying operation. The coloration obtained is light brown.

EXAMPLE 21

| Composition (A21) | |
|---|---|
| Identical to composition (A20) of Example 20. | |
| Composition (B21) | |
| Mixture (80/20) of cetylstearyl and cetylstearyl alcohols which are oxyethylenated [sic] with 33 moles of ethylene oxide, sold under the name LANOL CTO by the company SEPPIC | 2 g |
| Glycerine | 0.4 g |
| Glucose | 10 g |
| Glucose oxidase | 15,000 units |
| Horseradish peroxidase | 2,600 units |
| Orthophosphoric acid | qs pH = 7 |
| Demineralized water | qs 100 g |

The first composition is applied to a lock of hair, which is initially white, and is left in place for 15 minutes. The hair is rinsed. The second composition is applied and is left in place for 15 minutes. The procedure is completed by a final rinsing operation and a drying operation. The coloration obtained is chestnut.

EXAMPLE 22

| Composition (A22) | |
|---|---|
| Identical to composition (A20) of Example (20). | |
| Composition (B22) | |
| Lactic acid | 5 g |
| Lactate oxidase | 200 units |
| Horseradish peroxidase | 2,600 units |
| Monoethanolamine | qs pH = 7.5 |
| Demineralized water | qs 100 g |

The first composition is applied to hair which is initially white, and is left in place for 15 minutes. The hair is rinsed. The second composition is applied and is left in place for 45 minutes. The procedure is completed by a final rinsing operation and a drying operation. The coloration obtained is dark blond.

We claim:

1. A method of dyeing keratin fibers, comprising applying:

a first component containing, in an aqueous medium suitable for dyeing said keratin fibers, at least one compound of the formula

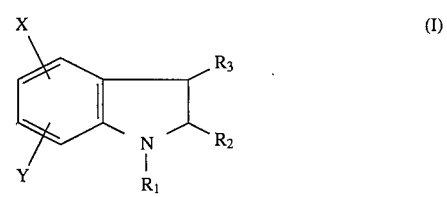 (I)

or

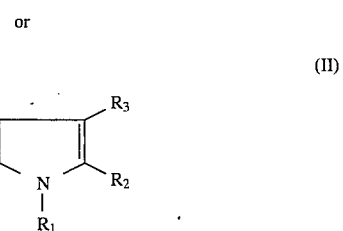 (II)

wherein $R_1$ denotes a hydrogen atom or a $C_1$–$C_4$ alkyl radical;

$R_2$ denotes a hydrogen atom, a $C_1$–$C_4$ alkyl or —COOH radical;

$R_3$ denotes a hydrogen atom or a $C_1$–$C_4$ alkyl radial;

X denotes a hydrogen atom, an $NH_2$, OH, $C_1$–$C_4$ alkyl or $C_1$–$C_4$ alkoxyl radial;

Y denotes an OH or $NH_2$ radical;

with the proviso that when X denotes an OH or alkyl radial, X occupies positions 5, 6 or 7 and X is in an ortho position relative to Y;

a second component containing, in an aqueous medium suitable for dyeing said keratin fibers, at least one peroxidase enzyme; and a third component containing, in a aqueous medium suitable for dyeing said keratinous fibers, at least hydrogen peroxide or an enzymatic source of hydrogen peroxide;

such that said first component is applied to said fibers first and separate from said third component.

2. The method of claim 1 wherein said first component contains an indole or indoline compound selected from the group consisting of 5,6-dihydroxyindole, 2-methyl-5,6-dihydroxylindole, 3-methyl-5,6-dihydroxyindole, 4-hydroxyindole, 2,3-dimethyl-5,6-dihydroxyindole, 6-hydroxy-5- methoxyindole, 6-hydroxyindole, 5-hydroxyindole, 7-hydroxyindole, 7-aminoindole, 5-amino-indole, 5,6-dihydroxyindole-2-carboxylic acid, 4-amino-indole, 1-methyl-5,6-dihydroxyindole, 5,6-dihydroxy-indoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline, 5-methoxy- 6-hydroxyindoline and the salts thereof.

3. The method according to claim 1 wherein said peroxidase enzyme is applied in amounts between 100 and 40,000 units per 100 g of the total amount of said first, second and third components.

4. The method according to claim 1 wherein the pH of said first, second and third components ranges from 3 to 10.

5. The method according to claim 1 wherein said enzymatic source of hydrogen peroxide consists of at least one natural substrate and at least one oxidase enzyme which catalyzes said at least one natural substrate to produce said enzymatic source of hydrogen peroxide; said at least one natural substrate and at least on oxidase enzyme forming a substrate/enzyme system.

6. The method according to claim 5 wherein said substrate/enzyme system is selected from the group consisting of glucose/glucose oxidase, galactose/galactose oxidase, pyranose/pyranose oxidase, L-sorbose/L-sorbose oxidase, ethanol/alcohol oxidase (1.1.3.13), isopropanol/secondary alcohol oxidase (1.1.3.18), pyruvic acid/pyruvate oxidase, oxalic acid/oxalate oxidase, aspartic acid/aspartate oxidase, glutamic acid/L-glutamate oxidase, uric acid/uricase, lactic acid/lactate oxidase, and mixtures thereof.

7. The method according to claim 5 wherein said substrate/enzyme system is present in an amount of between 100 and 20,000 catalytic units of oxidase per 100 g of the total amount of said first, second and third components.

8. The method according to claim 1 wherein said first component is applied to said keratin fibers in a first step in a composition (A) followed by application of said second and third components in a second step in a composition (B), said first and second steps being optionally separated by an intermediate rinsing operation.

9. The method according to claim 8, wherein said composition (A) is applied to said keratin fibers for a period ranging from 20 second to 20 minutes when said third component contains hydrogen peroxide or for a period ranging from 1 minute to 1 hour when said third component contains an enzymatic source of hydrogen peroxide; and said composition (B) is applied to said keratin fibers for a period ranging from 1 minute to 1 hour.

10. The method according to claim 1 wherein said first and said second components are applied to said keratin fibers, in a first step, in a composition (C) followed by application of said third component, in a second step, in a composition (D).

11. The method according to claim 10 wherein said composition (C) is applied to said keratin fibers for a period ranging from 20 seconds to 20 minutes; and said composition (D) is applied to said keratin fibers for a period ranging from 1 minute to 1 hour.

12. The method according to claim 1 wherein, in a first step, said first component is applied to said keratin fibers in a composition (E) followed by the application to said keratin fibers of said second component in a composition (F) followed by the application to said keratin fibers in a third step of said third component in a composition (G).

13. The method according to claim 12, wherein said composition (E) and composition (F) are applied to said keratin fibers for a period ranging from 20 seconds to 20 minutes, and said composition (G) is applied to said keratin fibers for a period ranging from 1 minute to 1 hour.

14. The method according to claim 1 further comprising rinsing and drying said keratin fibers subsequent to applying said first, second and third components.

15. The method according to claim 8 wherein the compound of formula (I) or (II) is present in an amount of between 0.2 and 5% by weight relative to the total weight of said composition (A).

16. The method according to claim 10 wherein the compound of formula (I) or (II) is present in an amount of between 0.2 and 5% by weight relative to the total weight of composition (C).

17. The method according to claim 12 wherein the compound of formula (I) or (II) is present in an amount of between 0.2 and 5% by weight relative to the total weight of composition (E).

18. The method according to claim 8 wherein said hydrogen peroxide is present in an amount of between 0.03 and 10% by weight relative to the total weight of composition (B).

19. The method according to claim 10 wherein the compound of formula (I) or (II) is present in an amount of between 0.2 and 5% by weight relative to the total weight of composition (D).

20. The method according to claim 12 wherein the compound of formula (I) or (II) is present in an amount of between 0.2 and 5% by weight relative to the total weight of composition (G).

21. The method according to claim 5 wherein said natural substrate is present in an amount of between 1 and 25% by weight relative to the total weight of said second component or said third component.

22. The method according to claim 5 wherein said natural substrate is present in an amount of between 1 and 25% by weight relative to the total weight of said second and third components.

23. The method according to claim 8 wherein said composition (A) further contains at least an oxidation dye, a coupling agent or a direct dye.

24. The method according to claim 10 wherein said composition (C) further contains at least an oxidation dye, a coupling agent or a direct dye.

25. The method according to claim 12 wherein said composition (E) further contains at least an oxidation dye, a coupling agent or a direct dye.

26. The method according to claim 8 wherein said composition (A) further contains a solvent selected from the group consisting of lower alcohols, glycol ethers, glycol esters, glycols and lower esters.

27. The method according to claim 10 wherein said composition (C) further contains a solvent selected from the group consisting of lower alcohols, glycol ethers, glycol esters, glycols and lower esters.

28. The method according to claim 12 wherein said composition (E) further contains a solvent selected from the group consisting of lower alcohols, glycol ethers, glycol esters, glycols and lower esters.

29. The method according to claim 8 wherein at least one of composition (A) and (B) further contains at least one of adjuvants, thickening agents, fragrances, sequestering agents, treatment agents, dispersing agents, or agents for swelling keratin fibers.

30. The method according to claim 10 wherein at least one of composition (C) and (D) further contains at least one of adjuvants, thickening agents, fragrances, sequestering agents, treatment agents, dispersing agents or agents for swelling keratin fibers.

31. The method according to claim 12 wherein at least one of composition (E), (F) and (G) further contains at least one of adjuvants, thickening agents, fragrances, sequestering agents, treatment agents, dispersing agents, or agents for swelling keratin fibers.

32. The method according to claim 8 wherein the pH of compositions (A) and (B) ranges from 4.5 to 7.5.

33. The method according to claim 10 wherein the pH of compositions (C) and (D) ranges from 4.5 to 7.5.

34. The method according to claim 12 wherein the pH of compositions (E), (F) and (G) ranges from 4.5 to 7.5.

35. A multi-component device or dyeing kit comprising first and second compartments containing said compositions (A) and (B) of claim 8, respectively.

36. A multi-component device or dyeing kit comprising a first and second compartments containing said compositions (C) and (D) of claim 10, respectively.

37. A multi-component device or dyeing kit comprising a first, second and third compartments containing said compositions (E), (F) and (G) of claim 12, respectively.

* * * * *